United States Patent [19]

Keijsper et al.

[11] Patent Number: 5,243,079
[45] Date of Patent: Sep. 7, 1993

[54] NOVEL HEXAKIS PHOSPHINE CATALYST

[75] Inventors: Johannes J. Keijsper; Alexander W. van der Made; Petrus W. N. M. van Leeuwen, all of Amsterdam, Netherlands

[73] Assignee: Shell Oil Company, Houston, Tex.

[21] Appl. No.: 936,491

[22] Filed: Aug. 28, 1992

Related U.S. Application Data

[62] Division of Ser. No. 684,110, Apr. 12, 1991, Pat. No. 5,169,926.

[30] Foreign Application Priority Data

May 10, 1990 [NL] Netherlands ................. 9001114

[51] Int. Cl.$^5$ .............................................. C07F 9/02
[52] U.S. Cl. ........................................ 568/13; 568/17
[58] Field of Search ....................................... 568/13, 17

[56] References Cited

U.S. PATENT DOCUMENTS

| | | |
|---|---|---|
| 3,694,412 | 9/1972 | Nozaki . |
| 4,818,810 | 4/1989 | Drent . |
| 4,820,802 | 4/1989 | Drent et al. . |
| 4,835,250 | 5/1989 | Drent . |
| 4,843,144 | 6/1989 | Van Broekhoven et al. . |
| 4,868,282 | 9/1989 | Van Broekhoven et al. . |
| 4,880,903 | 11/1989 | Van Broekhoven et al. . |
| 5,057,599 | 10/1991 | Wong . |
| 5,102,844 | 4/1992 | Wong . |

FOREIGN PATENT DOCUMENTS

| | | |
|---|---|---|
| 121965 | 10/1984 | European Pat. Off. . |
| 181014 | 5/1986 | European Pat. Off. . |
| 213671 | 3/1987 | European Pat. Off. . |
| 257663 | 3/1988 | European Pat. Off. . |

Primary Examiner—Marianne M. Cintins
Assistant Examiner—Margaret J. Page

[57] ABSTRACT

An improved process for the production of linear alternating polymers of carbon monoxide and at least one ethylenically unsaturated hydrocarbon employs a novel catalyst composition formed from a compound of palladium, the anion of a strong non-hydrohalogenic acid and a novel hexakis phosphine ligand. The process is characterized by a lessened degree of reactor fouling.

6 Claims, No Drawings

NOVEL HEXAKIS PHOSPHINE CATALYST

This is a division, of application Ser. No. 07/684,110, filed Apr. 12, 1991 now U.S. Pat. No. 5,169,926.

FIELD OF THE INVENTION

This invention relates to an improved process for the production of linear alternating polymers of carbon monoxide and at least one ethylenically unsaturated hydrocarbon. More particularly, the invention relates to such a polymerization process which employs a novel catalyst composition formed from, inter alia, a novel hexakis phosphine ligand.

BACKGROUND OF THE INVENTION

The class of linear alternating polymers of carbon monoxide and at least one ethylenically unsaturated hydrocarbon has been known for some time. Nozaki, e.g., U.S. Pat. No. 3,694,412, produced such polymers in the presence of arylphosphine complexes of palladium moieties and certain inert solvents. More recent methods of producing such polymers are illustrated by a number of published European Patent Applications including Nos. 121,965, 181,014, 213,671 and 257,663. The processes involve polymerization in the presence of a catalyst formed from a compound of palladium, cobalt or nickel, the anion of a strong non-hydrohalogenic acid and a bidentate ligand of phosphorus, arsenic, antimony or nitrogen.

The linear alternating polymers, now known as polyketones or polyketone polymers, are relatively high molecular weight materials having established utility as premium thermoplastics. They are processed by methods conventional for thermoplastic polymers such as extrusion, injection molding and thermoforming into a variety of shaped articles such as containers for food or drink.

One method of polymerizing the carbon monoxide and at least one ethylenically unsaturated hydrocarbon comprises a batch process in a suitable reactor which is preferably equipped with some agitation means to promote reactant/catalyst contact. In such a process the reactants, catalyst composition and a reaction diluent are charged to the reactor and maintained under polymerization conditions. In an alternate semi-continuous process, reactants are continuously charged to the reactor until the viscosity of the resulting suspension of polymer product in the reaction diluent becomes too great to permit efficient heat removal. At this point, the reaction is terminated and the polymer suspension is removed.

A problem particularly associated with such batch or semi-continuous operation is a tendency toward reactor fouling. During the polymerization, there is a tendency for polymer to deposit upon the inner surfaces of the reactor such as the reactor walls, baffles, stirrer blades, stirring shaft and cooling and heating coils. This deposited polymer is difficult to remove by methods such as washing with reaction diluent. It is frequently necessary to employ mechanical methods. The reactor fouling can be as high as 50% or greater and is a substantial detriment to commercial operation of the process. It would be of advantage to provide a method of producing the linear alternating polymers with less reactor fouling.

SUMMARY OF THE INVENTION

The present invention provides an improved process for the production of linear alternating polymers of carbon monoxide and at least one ethylenically unsaturated hydrocarbon. More particularly, the invention provides a process for the production of such polymers which employs a novel catalyst composition formed from, among other catalyst composition precursors, a novel hexakis phosphine ligand. The process is characterized by a reduced degree of reactor fouling.

DESCRIPTION OF THE INVENTION

The process of the invention employs a catalyst composition formed from, in part, a hexakis phosphine ligand. In contrast with the bidentate ligands of the above published European Patent Applications and tetrakis phosphine ligands of copending U.S. application Ser. No. 503,414, filed Mar. 30, 1990, now U.S. Pat. No. 5,057,599, the hexakis phosphine ligands are employed to form catalyst compositions used to catalyze the process of producing the linear alternating polymers, in which process a considerably reduced level of reactor fouling is observed.

The ethylenically unsaturated hydrocarbons useful as precursors of the polyketone polymers have up to 20 carbon atoms inclusive, preferably up to 10 carbon atoms inclusive, and are aliphatic such as ethylene and other $\alpha$-olefins including propylene, butylene, isobutylene, 1-hexene, 1-octene and 1-dodecene, or are arylaliphatic containing an aryl substituent on an otherwise aliphatic molecule, particularly an aryl substituent on a carbon atom of the ethylenic unsaturation. Illustrative of this latter class of ethylenically unsaturated hydrocarbons are styrene, p-methylstyrene, p-ethylstyrene and m-isopropylstyrene. The preferred copolymers produced according to the invention are copolymers of carbon monoxide and ethylene. The preferred terpolymers are terpolymers of carbon monoxide, ethylene and a second ethylenically unsaturated hydrocarbon of at least 3 carbon atoms, particularly an $\alpha$-olefin such as propylene.

When the preferred terpolymers are produced by the process of the invention, there will be at least about 2 units incorporating a moiety of ethylene for each unit employing a moiety of the second hydrocarbon. Preferably, there will be from about 10 units to about 100 units incorporating a moiety of ethylene for each unit incorporating a moiety of the second hydrocarbon. The polymer chain of the preferred polyketone polymers is therefore represented by the repeating formula

 (I)

wherein G is the moiety of the second ethylenically unsaturated hydrocarbon of at least 3 carbon atoms and the ratio of y:x is no more than about 0.5. When the preferred copolymers are produced, there will be no second hydrocarbon present and the polymer chain is represented by the above formula I wherein y is zero. When y is other than zero, i.e., terpolymers are produced, the $+CO-CH_2-CH_2+$ units and the $-CO+G+$ units occur randomly throughout the polymer chain and the preferred ratios of y:x are from about 0.01 to about 0.1. The end groups or "caps" of the polymer chain will depend upon what materials were present during polymerization and whether and how the polymer was purified. The precise nature of the end groups is of little significance so far as the overall properties of the polymer are concerned so that the polymer is fairly represented by the polymer chain as depicted above.

Of particular interest are the linear alternating polymers having a number average molecular weight from about 1000 to about 200,000, particularly those polymers of number average molecular weight from about 20,000 to about 90,000, as determined by gel permeation chromatography. The properties of the polymers will depend in part on the molecular weight, whether the polymer is a terpolymer or a copolymer and, in the case of terpolymers, the nature of and the proportion of the second hydrocarbon present. Such polymers will typically have a melting point from about 175° C. to about 300° C., more often from about 210° C. to about 270° C. The polymers will have a limiting viscosity number (LVN), as determined in a standard capillary viscosity measuring device in m-cresol at 60° C., of from about 0.4 dl/g to about 10 dl/g, preferably from about 0.8 dl/g to about 4 dl/g.

The polymers are produced by the general procedures of the above published European Patent Applications. Although the scope of the polymerization process is extensive, preferred catalyst compositions are formed from a compound of palladium, the anion of a non-hydrohalogenic acid having a pKa below 2 and a ligand of phosphorus. The compound of palladium is a palladium carboxylate, particularly a palladium alkanoate, and compounds such as palladium acetate, palladium propionate, palladium butyrate, palladium hexanoate and palladium octanoate are satisfactory. Palladium acetate is a particularly preferred compound of palladium.

The anion precursor of the catalyst composition is the anion of a non-hydrohalogenic acid having a pKa below about 2. Suitable acids include inorganic acids such as sulfuric acid or perchloric acid and organic acids including carboxylic acids such as trichloroacetic acid, dichloroacetic acid, trifluoroacetic acid or difluoroacetic acid as well as sulfonic acids such as methanesulfonic acid, trichloromethanesulfonic acid and p-toluenesulfonic acid. The preferred anion is the anion derived from trifluoroacetic acid or p-toluenesulfonic acid, particularly trifluoroacetic acid. The anion is preferably provided as the free acid but alternatively is provided as a metal salt, particularly as a non-noble transition metal salt. However provided, the quantity of anion to be employed is from about 1 mole to about 100 moles per mole of palladium. Preferably, the anion is provided in a quantity from about 2 moles to about 50 moles per mole of palladium.

The hexakis phosphine ligand is a compound containing 6 phosphorus-containing groups arranged around an aromatic ring central portion. The phosphorus-containing groups contain 2 monovalent aromatic substituents and are connected to the central ring by a propoxymethyl linking group. Illustrative of the hexakis phosphine ligands of the invention are compounds of the formula

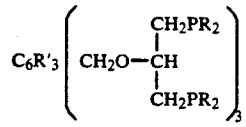

wherein $C_6$ represents a benzene ring, R' independently is hydrogen or lower alkyl of up to 4 carbon atoms inclusive and R independently is aromatic of up to 10 carbon atoms. The R group is hydrocarbon containing only atoms of carbon and hydrogen, e.g., phenyl, tolyl or naphthyl, or is substituted hydrocarbon containing additional atoms in the form of polar aromatic ring substituents at least one of which is located on an aromatic ring carbon atom ortho to the ring carbon atom through which the R group is attached to the phosphorus atom. Preferred R groups are alkoxyphenyl with at least one alkoxy group on an aromatic ring carbon ortho to the ring atom connecting the R group to the phosphorus. Illustrative of such R groups are 2-methoxyphenyl, 2-ethoxyphenyl, 2,6-dipropoxyphenyl, 2,4-dimethoxyphenyl and 2,4,6-triethoxyphenyl. Particularly preferred as the R group is 2-methoxyphenyl. The R' groups are preferably hydrogen or methyl.

The spatial arrangement of the R' and the bisphosphinopropoxymethyl groups around the central benzene ring is not critical, but it is preferred that like groups not be on adjacent ring carbon atoms so that the three bisphosphinopropoxymethyl groups are preferably in a 1,3,5 relationship. Illustrative of such preferred compounds are 1,3,5-tris{[1,3-bis(di(2-methoxyphenyl)-phosphino)-2-propoxy]methyl}benzene and 1,3,5-tris{[1,3-bis(di(2-methoxyphenyl)phosphino)-2-propoxy]methyl}-2,4,6-trimethylbenzene.

The compounds of the above formula II are novel compounds but are produced by known methods which will depend upon whether the R' groups are hydrogen or alkyl. When R' is hydrogen, the compounds are illustratively produced by brominating mesitylene and reacting the resulting tri(bromomethyl)benzene with epibromohydrin to produce a 1,3,5-tris(1,3-dibromo-2-propoxymethyl)benzene. This product is in turn reacted with a tri(2-alkoxyphenyl)phosphine in the presence of sodium to produce the compound of the above formula II wherein each R' is hydrogen and each R is 2-alkoxyphenyl. To obtain a compound of formula II wherein R' is alkyl, e.g., methyl, mesitylene is reacted with formaldehyde and hydrobromic acid to produce 1,3,5-tri(-bromomethyl)-2,4,6-trimethylbenzene. This product is illustratively converted to the hexakis phosphine (formula II) in the same manner.

In the formation of the catalyst composition, the quantity of the hexakis phosphine compound to be used is from about 0.1 mole to about 1.0 mole per mole of palladium. Preferred quantities of hexakis phosphine compound are from about 0.2 mole to about 0.5 mole per mole of palladium.

The polymerization is conducted by contacting the carbon monoxide and hydrocarbon in a suitable reactor under polymerization conditions in the presence of a reaction diluent and a catalytic quantity of the catalyst composition. Suitable reaction diluents include the lower alkanols such as methanol or ethanol and the lower alkanones such as acetone or methyl ethyl ketone. The molar ratio of carbon monoxide to total ethylenically unsaturated hydrocarbon is from about 10:1 to about 1:10 but preferably from about 5:1 to about 1:5. The catalyst composition is formed by mixing the components which is usefully accomplished prior to introduction into the polymerization reactor or alternatively the catalyst composition is formed in situ in the reactor by adding the individual components. Sufficient catalyst composition is employed to provide from about $1 \times 10^{-7}$ mole to about $1 \times 10^{-3}$ mole of palladium per mole of total ethylenically unsaturated hydrocarbon although quantities of catalyst composition sufficient to provide from about $1 \times 10^{-6}$ mole to about $1 \times 10^{-4}$ mole of palladium per mole of total unsaturated hydrocarbon are preferred. Typical polymerization conditions include a reaction temperature from about 25° C. to about 150° C., but reaction temperatures from about 30° C. to about 130° C. are more frequently employed. Suitable reaction pressures are from about 2 bar to about 150 bar and particularly from about 5 bar to about 100 bar. Reactant/catalyst composition contact is facilitated by some method of agitation such as shaking or stirring. Subsequent to polymerization the reaction is terminated as by cooling the reactor and contents and releasing the pressure. The polyketone product is typically obtained as a suspension in the reaction diluent. The product is recovered by conventional methods such as filtration or centrifugation and is purified if desired by contact with a solvent or complexing agent selective for catalyst residues.

In the polymerization process, a portion of the polyketone product is not removed as the polymer suspension but remains in the reactor upon suspension removal as a deposit upon the inner surfaces of the reactor such as the reactor walls below the liquid level, the baffles and stirring blades and shaft and upon heating and cooling coils. This reactor fouling is not overcome by washing with reaction diluent and generally requires some mechanical method of removal. The fouling results in a diminished yield of recoverable polymer as well as a greater down time of the reactor for removal of the deposits. It is an advantage of the process of the present invention using a catalyst composition formed from, inter alia, the hexakis phosphine ligand that a considerably reduced degree of reactor fouling is observed with a corresponding increase in the economy of the polymerization process.

The invention is further illustrated by the following Comparative Examples (not of the invention) and the following Illustrative Embodiments which should not be regarded as limiting. In the Illustrative Embodiments and Comparative Examples, all carbon monoxide/ethylene/propylene terpolymers were found by $^{13}$C-NMR analysis to be linear alternating polymers.

ILLUSTRATIVE EMBODIMENT I

The compound 1,3,5-tri(bromomethyl)benzene was produced by boiling under reflux, with stirring, a mixture of 0.5 mol mesitylene, 1.6 mol N-bromosuccinimide, 50 mg dibenzoyl peroxide and 1.3 liter carbon tetrachloride while irradiating the mixture with a 375 watt photographic lamp. After the mixture was cooled and filtered, the mixture was washed successively with aqueous sodium bicarbonate solution and then twice with water. The resulting mixture was dried over magnesium sulfate and concentrated to 400 ml. Petroleum ether (boiling range 60° C. to 85° C.) was then added and the mixture was stored at 0° C. The crystals which formed were removed by filtration and purified by repeated recrystallization from a mixture of trichloromethane and petroleum ether. The yield of 1,3,5-tri(bromomethyl)benzene was 40 g, 23%.

ILLUSTRATIVE EMBODIMENT II

The compound 1,3,5-tri(bromomethyl)-2,4,6-trimethylbenzene was produced by rapidly adding 70 ml of a 31% solution of hydrobromic acid in acetic acid to a mixture of 12.0 g (0.10 mol) mesitylene, 10.0 g (0.33 mol) paraformaldehyde and 50 ml of 99.7% glacial acetic acid. The resulting mixture was heated in a period of 1 hour to 90° C. and maintained at that temperature for 8 hours. After the mixture was cooled, the solid material that formed was removed by filtration and washed with pentane. The yield of 1,3,5-tri(bromomethyl)-2,4,6-trimethylbenzene was 36.3 g, 91%. By using the mother liquor in a subsequent preparation, the yield was increased to almost 100%.

ILLUSTRATIVE EMBODIMENT III

The compound 1,3,5-tris[(1,3-dibromo-2-propoxy)methyl]benzene was produced by heating a mixture of 24.6 g (0.18 mol) epibromohydrin, 20.22 g (0.0567 mol) of 1,3,5-tri(bromomethyl)benzene and 20 mg of mercuric dichloride for 9 hours at 160° C. After adding an additional 3.4 g (0.024 mol) epibromohydrin the mixture was heated for 4 hours at 160° C. The excess epibromohydrin was then removed by distillation under reduced pressure. The yield of 1,3,5-tris[(1,3-dibromo-2-propoxy)methyl]benzene was 37 g, 85%.

ILLUSTRATIVE EMBODIMENT IV

The compound 1,3,5-tris[(1,3-dibromo-2-propoxy)methyl]-2,4,6-trimethylbenzene was prepared by heating a mixture of 9.27 g epibromohydrin, 7.5 g 1,3,5-tri(bromomethyl)-2,4,6-trimethylbenzene and 10 mg of mercuric chloride for 12 hours at 160° C. The reaction mixture was cooled and washed with pentane to give 13.2 g of 1,3,5-tris[(1,3-dibromo-2-propoxy)methyl]-2,4,6-trimethylbenzene, a 10% yield.

ILLUSTRATIVE EMBODIMENT V

The compound 1,3,5-tris{[1,3-bis(di(2-methoxyphenyl)phosphino)-2-propoxy]methyl}benzene was produced by a number of process steps conducted under nitrogen. To 125 ml of dry liquid ammonia maintained at −78° C. was added 0.4 g (17.5 mmol) sodium, 3.1 g (8.75 mmol) tri(2-methoxyphenyl)phosphine and 12.5 ml tetrahydrofuran which had been dried over sodium. After the mixture was stirred for 6 hours at −78° C., 0.467 g (8.75 mmol) ammonium chloride was added. After an additional 30 minutes 4.3 mmol of 1,3,5-tris[(1,3-dibromo-2-propoxy)methyl]benzene was added. The ammonia was then removed by evaporation and the solvent removed under reduced pressure. The solid residue was dissolved in 50 ml dichloromethane and washed with 50 ml of a 5% aqueous solution of ammonium chloride. The solvent was removed and 50 ml of tetrahydrofuran was added. The solution was then filtered, concentrated to 10 ml and 50 ml of methanol was added. The yield of the desired hexakis phosphine was 1.2 g (48%).

ILLUSTRATIVE EMBODIMENT VI

The compound 1,3,5-tris{[1,3-bis(di(2-methoxyphenyl)phosphino)-2-propoxy]methyl}-2,4,6-trimethylbenzene was produced by a procedure substantially similar to that of Illustrative Embodiment V except that 1,3,5-tris-[(1,3-dibromo-2-propoxy)methyl]-2,4,6- trimethylbenzene was used instead of 1,3,5-tris[(1,3-dibromo-2-propoxy)methyl]benzene. The yield of the desired hexakis phosphine was 95%.

COMPARATIVE EXAMPLE I

A terpolymer of carbon monoxide, ethylene and propylene was produced by charging to an autoclave of 300 ml capacity equipped with a mechanical stirrer 135 ml methanol, 4 ml acetone, 0.009 mmol palladium acetate, 0.19 mmol trifluoroacetic acid and 0.01 mmol 1,3-bis[di(2-methoxyphenyl)phosphino]propane. The air in the autoclave was excluded by pressurizing the autoclave to 50 bar with carbon monoxide three times and then each time releasing the pressure. The autoclave and contents were then warmed to 82° C. and carbon monoxide was introduced to give a pressure of 25 bar followed by propylene to give a pressure of an additional 10 bar and ethylene to give an additional pressure of 15 bar. During polymerization the pressure was maintained at 52 bar by the addition of an equimolar mixture of carbon monoxide and ethylene. After 8.2 hours the reaction was terminated by cooling the autoclave and contents to room temperature and then releasing the pressure. A polymer suspension was removed from the reaction and found to contain 12.3 g of terpolymer and 12.4 g of polymer remained in the reactor. The degree of reactor fouling was therefore calculated to be 12.3/12.3+12.4 or 50%. The polymerization rate was calculated to be 3.1 kg of terpolymer/g Pd hr.

COMPARATIVE EXAMPLE II

A carbon monoxide/ethylene/propylene terpolymer was prepared by a procedure substantially similar to that of Comparative Example I except that 0.01 mmol 1,3-bis{[1,3-bis(di(2-methoxyphenyl)phosphino)-2-propoxy]methyl}benzene was used instead of 1,3-bis[di(2-methoxyphenyl)phosphino]propane, the reaction temperature was 77° C. instead of 82° C. and the reaction time was 3.5 hours instead of 8.2 hours. The polymer suspension contained 10.0 g of terpolymer while 7.9 g of terpolymer remained within the reactor. The reactor fouling was therefore calculated to be 44%, and the calculated rate of polymer production was 5.3 kg of terpolymer/g Pd hr.

COMPARATIVE EXAMPLE III

A carbon monoxide/ethylene/propylene terpolymer was produced by a procedure substantially similar to that of Comparative Example I except that 0.005 mmol of 1,4-bis{[1,3-bis(bis(di(2-methoxyphenyl)phosphino)-2-propoxy]methyl}benzene was used instead of 1,3-bis[di(2-methoxyphenyl)phosphino]propane, the reaction temperature was 80° C. instead of 82° C. and the reaction time was 2.7 hours instead of 8.2 hours. The polymer suspension contained 12.8 g of terpolymer while 6.1 g terpolymer remained in the reaction. The degree of reactor fouling was calculated as 32% and the polymerization rate was 7.3 kg terpolymer/g Pd hr.

ILLUSTRATIVE EMBODIMENT VII

A terpolymer of carbon monoxide, ethylene and propylene was prepared by a procedure substantially similar to that of Comparative Example I except that 0.003 mmol of 1,3,5-tris{[1,3-bis(di(2-methoxyphenyl)phosphino)2-propoxy]methyl}benzene was used instead of 1,3-bis[di(2-methoxyphenyl)phosphino]propane, the reaction temperature was 80° C. instead of 82° C. and the reaction time was 2.7 hours instead of 8.2 hours. The polymer suspension contained 8.7 g of terpolymer while 0.3 g remained in the reactor. The degree of reactor fouling was calculated to be 3% and the calculated rate of terpolymer production was 3.5 kg of terpolymer/g Pd hr.

ILLUSTRATIVE EMBODIMENT VIII

A terpolymer of carbon monoxide, ethylene and propylene was produced by a procedure substantially similar to that of Comparative Example I except that 0.003 mmol of 1,3,5-tris{[1,3-bis(di(2-methoxyphenyl)phosphino)-2-propoxy]methyl}-2,4,6-trimethylbenzene was used instead of 1,3-bis[di(2-methoxyphenyl)phosphino]propane, the reaction temperature was 85° C. instead of 82° C., and the reaction time was 5.2 hours instead of 8.2 hours. The polymer suspension contained 13.7 g of terpolymer while 1.5 g of terpolymer remained in the reactor. The degree of reactor fouling was calculated to be 10% and the calculated reaction rate was 3.1 kg of terpolymer/g Pd hr.

What is claimed is:

1. The hexakis phosphine compound of the formula

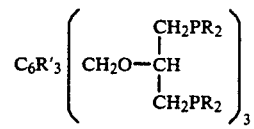

wherein $C_6$ represents a benzene ring, R' independently is hydrogen or lower alkyl of from 1 to 4 carbon atoms, and R independently is alkoxyphenyl wherein at least one alkoxy group is substituted on a carbon atom ortho to the carbon atom through which R is connected to phosphorus.

2. The compound of the claim 1 wherein the

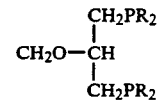

groups are located in positions 1, 3, and 5 on the benzene ring.

3. The compound of claim 2 wherein R is 2-alkoxyphenyl.

4. The compound of claim 2 wherein R is 2-methoxyphenyl.

5. The compound of claim 4 wherein R' is hydrogen.

6. The compound of claim 4 wherein R' is methyl.

* * * * *